United States Patent [19]
Wall et al.

[11] Patent Number: 5,932,588
[45] Date of Patent: Aug. 3, 1999

[54] CAMPTOTHECIN COMPOUNDS WITH COMBINED TOPOISOMERASE I INHIBITION AND DNA ALKYLATION PROPERTIES

[75] Inventors: Monroe E. Wall, Chapel Hill; Mansukh C. Wani, Durham, both of N.C.

[73] Assignee: Research Triangle Institute, Research Triangle Park, N.C.

[21] Appl. No.: 08/946,701

[22] Filed: Oct. 8, 1997

Related U.S. Application Data

[63] Continuation of application No. 08/561,664, Nov. 22, 1995, abandoned.

[51] Int. Cl.$^6$ ..................... A61K 31/395; C07D 491/147
[52] U.S. Cl. ............................................. 514/279; 546/71
[58] Field of Search ................................ 514/279; 546/41

[56] References Cited

U.S. PATENT DOCUMENTS

| | | | |
|---|---|---|---|
| 4,031,098 | 6/1977 | Sugasawa et al. | 546/48 |
| 4,473,692 | 9/1984 | Miyasaka et al. | 546/48 |
| 4,545,880 | 10/1985 | Miyasaka et al. | 204/158 |
| 4,604,463 | 8/1986 | Miyasaka et al. | 546/48 |
| 4,894,456 | 1/1990 | Wall et al. | 546/48 |
| 4,914,205 | 4/1990 | Sawada et al. | 546/70 |
| 4,943,579 | 7/1990 | Vishnuvajjala et al. | 514/283 |
| 4,981,968 | 1/1991 | Wall et al. | 546/41 |
| 5,049,668 | 9/1991 | Wall et al. | 546/4 B |
| 5,053,512 | 10/1991 | Wani et al. | 546/41 |
| 5,106,742 | 4/1992 | Wall et al. | 435/233 |
| 5,122,526 | 6/1992 | Wall et al. | 514/283 |
| 5,122,606 | 6/1992 | Wani et al. | 514/279 |
| 5,180,722 | 1/1993 | Wall et al. | 546/41 |
| 5,225,404 | 7/1993 | Giovannella | 514/283 |
| 5,227,380 | 7/1993 | Wall et al. | 514/283 |
| 5,244,903 | 9/1993 | Wall et al. | 514/279 |
| 5,340,817 | 8/1994 | Wall et al. | 514/279 |
| 5,342,947 | 8/1994 | Lackey et al. | 546/41 |
| 5,364,858 | 11/1994 | Wall et al. | 514/279 |
| 5,496,830 | 3/1996 | Shapiro et al. | 514/283 |
| 5,559,235 | 9/1996 | Luzzio et al. | 546/41 |
| 5,646,159 | 7/1997 | Wall et al. | 514/279 |

FOREIGN PATENT DOCUMENTS

| | | |
|---|---|---|
| 0 074 256 | 3/1983 | European Pat. Off. . |
| 0 220 601 | 5/1987 | European Pat. Off. . |
| 0 540 099 | 5/1993 | European Pat. Off. . |
| 59-5188 | 1/1984 | Japan . |
| 59-51289 | 3/1984 | Japan . |
| 61-85319 | 4/1986 | Japan . |
| 61-85389 | 4/1986 | Japan . |
| WO/9602546 | 2/1996 | WIPO . |

OTHER PUBLICATIONS

Govindachari et al, *Indian J. Chem.*, vol. 10, pp. 453–454 (1972).
Pommier et al, *Proc. Natl. Acad. Sci. USA*, vol. 92, pp. 8861–8865 (1995).
Chemical Abstracts, vol. 92, No. 5, AN 37766e.
Chemical Abstracts, vol. 92, No. 3, AN 18799b.
Hertzberg et al, *Proc. Annu. Meet. Am. Assoc. Cancer Res.*, 1989, AN 30:A2485 (Abstract).
Ohno et al, *Proc. Annu. Meet. Am. Soc. Clin. Oncol.*, 1989, AN 8:A1010 (Abstract).
Hertzberg et al, *J. Med. Chem.*, vol. 32, pp. 715–720, 1989 (Abstract).
Yakult (1984).
Yakult (1982).
Index, Chemical Abstracts, vol. 84, p. 786, Compound 115631h (1976.
Paw et al Chemical Abstracts, vol. 84:115629p (1976).
Danishetsky et al, *J. Org. Chem.*, vol. 39, pp. 3430–3432 (1974).
Gilmour et al, *J. Mol. Cell. Biol.*, vol. 7, pp. 141–148 (1987).
Database WPI, Derwent Publications, Ltd., AN 89–179979/25, Dec. 1, 1987, EP 321 122.
Yang et al Chemical Abstracts, 100:13943w (1984).
Plattner et al, *J. Org. Chem.*, vol. 39, pp. 303–311 (1974).
Plattner et al, *J. Am. Chem. Soc.*, vol. 94, pp. 8613–8615 (1972).
Ronman et al, *J. of Lab. Com. and Radiopharm.*, vol. XVIII, pp. 319–329 (1979).
Nicholas et al, *J. Med. Chem.*, vol. 33, pp. 972–978 (1990).
Wani et al, *J. Med. Chem.*, vol. 23, pp. 554–560 (1980).
Wall et al, *J. Med. Chem.*, vol. 29, pp. 1553–1555 (1986).
Hsiang et al, *Cancer Research*, vol. 49, pp. 4385–4389 (1989).
Jaxel et al, *Cancer Research*, vol. 49, pp. 1465–1469 (1989).
Pommier et al, *Proc. Annu. Meet. Am. Assoc. Cancer Res.*, AN 29:A1080 (1988).
Hsiang et al, *Proc. Annu. Meet. Am. Assoc. Cancer Res.*, AN 30:A2476 (1989).
Hsiang et al, *J. Bio. Chem.*, vol. 260, pp. 14873–14878 (1985).
Wani et al, *J. Med. Chem.*, vol. 30, pp. 1774–1779 (1987).
Wani et al, *J. Med. chem.*, vol. 29, pp. 2358–2363 (1986).
Giovanella et al, *Science*, vol. 246, pp. 1046–1048 (1989).
Nagata et al, *Cancer Treatment Reports*, vol. 71, pp. 341–348 (1987).
Kingsbury et al Jour. Med Chem vol. 34 pp. 98–107, 1991.
Giovanella et al. Science vol. 246 pp. 1046–1048 (1989).
Barilero et al. Jour. Chromatography) vol. 575 pp. 275–280 (1992).
Wall et al J. Med Chem, vol. 29 pp. 1553–1555 (1986).
Wani et al J. Med Chem vol. 29 pp. 2358–2363 (1986).
Wani et al. J. Med Chem vol. 23 pp. 554–560 (1980).
Wall et al J. Med Chem vol. 36 pp. 2689–2700 (1993).
Pommier et. al. Chem. Abstr vol. 123 Entry 306083 (1995).

*Primary Examiner*—Donald G. Daus
*Attorney, Agent, or Firm*—Oblon, Spivak, McClelland, Maier & Neustadt, P.C.

[57] ABSTRACT

Camptothecin compounds having a —$CH_2$—L group are effective anti-tumor compounds. These compounds inhibit the enzyme topoisomerase I and DNA of associated topoisomerase I-DNA complexes.

4 Claims, No Drawings

CAMPTOTHECIN COMPOUNDS WITH COMBINED TOPOISOMERASE I INHIBITION AND DNA ALKYLATION PROPERTIES

This application is a Continuation of application Ser. No. 08/561,664, filed on Nov. 22, 1995, now abandoned.

BACKGROUND OF THE INVENTION

1. Field of the Invention

This invention relates to camptothecin compounds which inhibit the enzyme topoisomerase I and alkylate deoxyribonucleic acid (DNA) in association with topoisomerase I. Camptothecin compounds have the ring structure shown below.

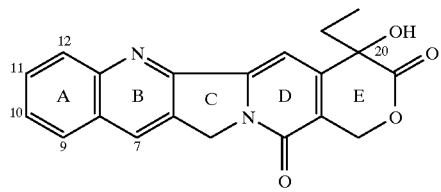

The invention also relates to the treatment of tumors in animals with camptothecin compounds.

2. Background of the Invention

Camptothecin (CPT) is a naturally occurring cytotoxic alkaloid which is known to inhibit the enzyme topoisomerase I and is a potent anti-tumor agent. Camptothecin was isolated from the wood and bark of Camptotheca acuminata by Wall et al. (Wall et al., 1966, J. Am. Chem. Soc., 88:3888).

U.S. Pat. No. 4,894,456 describes methods of synthesizing camptothecin compounds which act as inhibitors of topoisomerase I and are effective in the treatment of leukemia (L-1210). U.S. Pat. No. 5,225,404 discloses methods of treating colon tumors with camptothecin compounds.

Numerous camptothecin compounds and their use as inhibitors of topoisomerase I are taught by U.S. Pat. No. 5,053,512; U.S. Pat. No. 4,981,968; U.S. Pat. No. 5,049,668; U.S. Pat. No. 5,106,742; U.S. Pat. No. 5,180,722; U.S. Pat. No. 5,244,903; U.S. Pat. No. 5,227,380; U.S. Pat. No. 5,122,606; U.S. Pat. No. 5,122,526; and U.S. Pat. No. 5,340,817.

Naturally occurring camptothecin has the 20(S)-configuration and has been shown to inhibit both DNA and RNA synthesis and to cause reversible fragmentation of DNA in cultured mammalian cells (Hsiang et al., 1989, Cancer Research, 49:4385–4389). When the camptothecin is removed, the inhibition of high molecular weight RNA synthesis is reversed, whereas there was only a partial restoration of DNA synthesis.

The enzyme topoisomerase I has been identified as the cellular target of camptothecin compounds. The enzyme has been implicated in various DNA transactions such as replication, transcription and recombination. Topoisomerase I relaxes both positively and negatively supercoiled DNA. The enzyme mechanism is believed to involve a transient breakage of one of the two DNA strands and the formation of a reversible covalent topoisomerase I enzyme-DNA complex. Camptothecin interferes with the DNA breakage-reunion reaction by reversibly trapping the enzyme-DNA intermediate termed the "cleavable complex" by Hsiang et al., Id. The high levels of topoisomerase I in several types of human cancer and the low levels in correspondingly normal tissue provide the basis for tumor treatment with biologically active camptothecin analogs.

A need continues to exist, however, for camptothecin compounds having improved activity.

SUMMARY OF THE INVENTION

Accordingly, one object of the present invention is to provide camptothecin compounds having improved and novel biological activity.

This and other objects which will become apparent from the following description of exemplary embodiments have been achieved by the present camptothecin compounds which have combined topoisomerase I inhibition and DNA alkylating properties. The ability of the compounds of this invention to alkylate DNA in the topoisomerase I-DNA complex irreversibly is surprising.

DETAILED DESCRIPTION OF THE PREFERRED EMBODIMENTS

The camptothecin compounds of the present invention are characterized by the presence of a novel alkylating group at C7, C9, C10, C11 or C12 of the camptothecin ring structure. More specifically, the alkylating group is a group of the formula —$CH_2$—L, where L is a functional group which can be easily displaced, i.e. L is a good leaving group in nucleophilic substitution reactions. While not being bound by any particular theory, it is believed that nucleophilic groups on DNA displace leaving group L from the camptothecin compounds of the present invention resulting in alkylation of the DNA by the alkylating group of the camptothecin ring structure. Suitable nucleophilic groups present in DNA include the nucleophilic groups found in DNA bases adenine, guanine, thymine, and cytosine, such as $NH_2$, —NH— and =N— groups. When a camptothecin compound of the invention having a —$CH_2$—L group is contacted with DNA, nucleophilic displacement of leaving group L results in alkylation of the nucleic acid. The compounds of the present invention exhibit a novel anti-tumor activity by alkylating DNA.

Camptothecin compounds have an asymmetric carbon atom at the 20-position making two enantiomeric forms, i.e., the (R) and the (S) configurations, possible. This invention includes both enantiomeric forms and any combinations or mixtures of these forms. The invention also includes other forms of the camptothecin compounds including solvates, hydrates, polymorphs, salts, etc. Particularly preferred compounds are camptothecin derivatives having the (S) configuration at the 20-position.

U.S. Pat. No. 4,545,880 and JP 82/116,015 disclose camptothecin derivatives containing acyloxymethyl groups at the 7-position of the camptothecin ring structure. The compounds per se disclosed in these references are outside the scope of the present invention.

The term "alkyl" as used herein means a straight-chain or branched chain alkyl group with 1–30, preferably 1–18 carbon atoms, more preferably 1–8 carbon atoms, including methyl, ethyl, n-propyl, isopropyl, n-butyl, isobutyl, sec-butyl, tert-butyl, n-pentyl, isopentyl, n-hexyl, n-heptyl, n-octyl, 2-ethylhexyl, n-nonyl, n-decyl, undecyl, dodecyl, myristyl, heptadecyl and octadecyl groups. The term "alkyl" also includes cycloalkyl groups such as cyclopropyl, cyclopentyl, cyclohexyl, cycloheptyl and cyclooctyl groups.

The term "aryl" as used herein means a carbocyclic aromatic ring having 6–18 carbon atoms, preferably 6–10 carbon atoms in the aromatic ring structure. The aromatic rings may be substituted by one or more alkyl group, preferably alkyl groups having 1–10 carbon atoms. A particularly preferred aryl group is phenyl.

The term "aralkyl" as used herein means a straight-chain or branched chain alkyl group as defined above for the term "alkyl" bonded to an aryl group as defined above for the term "aryl". Preferred aralkyl groups are benzyl, phenethyl, etc.

As used herein, the term "acyl" means formyloxy and acyl moieties derived from aromatic carboxylic acids, heterocyclic carboxylic acids, aralkyl carboxylic acids, as well as alkyl and aromatic sulfonic acids. The alkyl groups of these acyloxy moieties may be a straight-chain or branched-chain alkyl group with 1–7 carbon atoms. Additionally, the acyl moiety may contain one or more unsaturated carbon—carbon bonds and may also carry one or more substituents such as halogen, amino and hydroxyl groups.

In the camptothecin compounds of the invention, the C7, C9, C10, C11 or C12 position bears the group —$CH_2$—L, where L is a good leaving group in nucleophilic substitution reactions. Suitable groups L include halogen (Cl, Br, I), $^+N_2$, $^+(OR^2)_2$ (where each $R^2$ independently is alkyl, aryl or aralkyl as defined above), $^+S(R^2)_2$, $^+N(R^2)_3$, $OC(O)R^2$, $OSO_2R^2$, $OSO_2CF_3$, and $OSO_2C_4F_9$.

The compounds of the present invention having the group —$CH_2$—L at C7 are generally prepared by the process described by Luzzio et al. (European Patent Application 540099A1, May 5, 1993; J. Med. Chem., 1995, 38:395) and in U.S. Pat. No. 5,053,512 involving Friedlander condensation of the appropriate synthon and a tricyclic ketone as shown below.

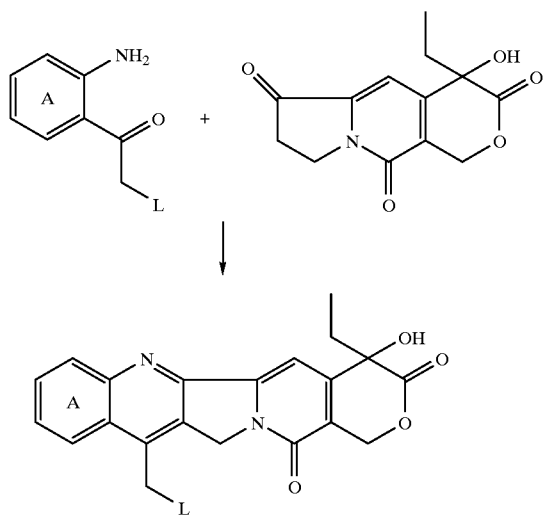

The compounds of the invention having the group —$CH_2$—L at C9, C10, C11 or C12 are prepared from known 20(S)-CPT compounds bearing a halogen, for example, a bromine atom, at the C9, C10, C11 or C12 position. The halogen atom can be readily converted into the corresponding cyano analog by reaction with CuCN, followed by hydrolysis to form the corresponding carboxy analog. The carboxy analog is reduced to the corresponding hydroxy methyl analog which can be reacted with $Ph_3P$—$CCl_4$ to provide the corresponding chloromethyl analog. The chloromethyl analog can be readily converted to the bromomethyl and iodomethyl analogs using LiBr or LiI. The remaining compounds of the invention are prepared from these compounds by reaction with the corresponding acid chloride, sulfonyl chloride, etc. These reactions are well known to one having ordinary skill in this art.

Camptothecin compounds for use in the method of the present invention include 20(S)-CPT and derivatives thereof in which the A ring is unsubstituted or there is a substituent at the 9-, 10-, 11-, 12-positions or a combination thereof or the 9- and 10,11-positions. Suitable compounds have the structure shown below.

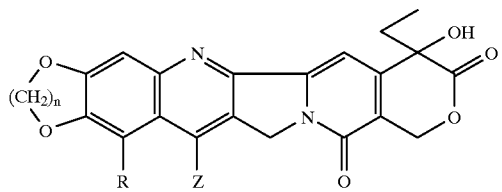

In the structure shown above, R is $NO_2$, $NH_2$, hydrogen, halogen (F, Cl, Br, I), COOH, OH, O—$C_{1-3}$ alkyl, SH, S—$C_{1-3}$ alkyl, CN, $CH_2NH_2$, NH—$C_{1-3}$ alkyl, $CH_2$—NH—$C_{1-3}$ alkyl, $N(C_{1-3}$ alkyl$)_2$, $CH_2N(C_{1-3}$ alkyl$)_2$, O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2N(C_{1-3}$ alkyl$)_2$, O—, NH— and S—$CH_2CH_2CH_2N(C_{1-3}$ alkyl$)_2$, CHO, $CH_2$—L or $C_{1-3}$ alkyl. Preferred compounds are those in which R is halogen, nitro, chloromethyl, bromomethyl, iodomethyl or amino. In the structure shown above, n is an integer of 1 or 2.

The lactone ring of the camptothecin compounds shown above may be opened by alkali metal or alkaline earth metal bases, for example, sodium hydroxide or calcium hydroxide to form alkali metal or alkaline earth metal salts of the open ring salt form of the camptothecin compounds. Open ring compounds have better solubility in water.

Additional camptothecin compounds which may be used in the method of the present invention are camptothecin compounds in which the hydroxyl group at the 20-position has been esterified to the α-carboxyl group of a naturally occurring amino acid to form a group of the formula —OC(O)—$(CH_2)_m$—$NR^3R^4$, where m=1–6 or —OC(O) $CHR^5NR^3R^4$, where $R^5$ is the side chain of one of the naturally occurring α-amino acids, $R^3$ and $R^4$ are, independently, hydrogen or $C_{1-8}$ alkyl. Suitable side chains $R^5$ are the side chains of the amino acids glycine, alanine, valine, leucine, isoleucine, phenylalanine, tyrosine, tryptophan, lysine, arginine, histidine, aspartate, glutamate, asparagine, glutamine, cysteine and methionine. Particularly preferred esters are glycinate esters. These esters are prodrugs which are converted to the camptothecin compound by hydrolysis of the ester bond. The esters may be prepared by the method described in U.S. Pat. No. 4,943,579 which is incorporated herein by reference for a more complete description of the process of preparing the esters and for a description of suitable esters formed by the process.

In the structure shown above, Z is —$CH_2$—L, or Z is H or alkyl when R is $CH_2$—L, where L is defined as follows: an electronegative functionality with the ability to be readily displaced by nucleophilic species. In the present invention, L may represent halogen (Cl, Br or I), or any OY group, where Y is a species which renders OY a leaving group toward nucleophilic displacement. Suitable Y groups include, but are not limited to, alkyl-C(=O)—, aryl-C (=O)—, alkyl-$SO_2$—, perfluoroalkyl-$SO_2$- and aryl-$SO_2$—, where alkyl and aryl are as defined above.

Other camptothecin compounds, which are preferably substituted in the 9- and/or 10- position, and can be used in the method of the present invention have the structure shown below.

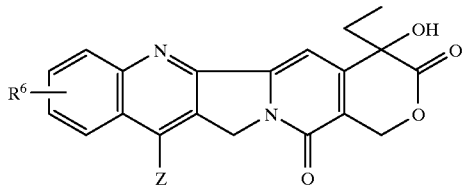

In this structure, $R^6$ is hydrogen, cyano, formyl, hydroxy, $C_{1-8}$ alkoxy, nitro, amino, halogen (I, Br, Cl, F), $C_{1-8}$ alkyl, trifluoromethyl, aminomethyl, azido, amido, hydrazino, $OC(O)R^7$, $OC(O)—NR^7R^8$ or $CH_2—L$, where $R^7$ and $R^8$ are, independently, hydrogen or $C_{1-8}$ alkyl. Z is the group —$CH_2$—L or Z is H or alkyl when $R^6$ is $CH_2$—L, where L is as defined above.

Compounds in which L is Br or I are readily prepared from the compound in which L is Cl by simple halide exchange employing LiBr or LiI in dimethylformamide (DMF) solution (Larock, R. C., Comprehensive Organic Transformations, VCH Publishers, Inc., p. 337, N.Y. 1989).

Alternatively, the 7-methyl compounds (L is H) can be prepared either by a Friedlander reaction employing the corresponding acetophenone, or by a free radical alkylation reaction (Sawada et al., 1991, Chem. Pharm. Bull., 39:2574). Free radical bromination of 7-methyl substrates can be accomplished by employing N-bromosuccinimide (NBS) in acetic acid (HOAc) under catalysis by benzoyl peroxide to give compounds in which L is Br.

Other compounds which possess oxygen-derived leaving groups, such as triflate or tosylate, are prepared from the 7-hydroxymethyl and/or 7-halomethyl compounds. The 7-hydroxymethyl compounds are prepared from the corresponding parent compounds by the hydroxymethylation reaction described by Sawada et al., 1991. Treatment of these compounds with readily available sulfonic acid chlorides or anhydrides using known procedures (Stang et al., 1982, Synthesis, 85) provides the highly electrophilic substrates noted above. Alternatively, the compounds described above can be generated from any of the substrates where L is Cl, Br or I by reaction with the silver salt of the corresponding acid (e.g., silver trifluoromethanesulfonate, silver tosylate, etc.) as described generally by Stang et al. and more specifically by Gramstad and Haszeldine (T. Gramstad and R. N. Haszeldine, 1956, J. Chem. Soc., 173).

The camptothecin compounds are administered in a dose which is effective to inhibit the growth of tumors. As used herein, an effective amount of the camptothecin compounds is intended to mean an amount of the compound that will inhibit the growth of tumors, that is, reduce the site of growing tumors relative to a control in which the tumor is not treated with the camptothecin compound. These effective amounts are generally from about 1–60 mg/kg of body weight per week, preferably about 2–20 mg/kg per week.

The compounds of the present invention may be administered as a pharmaceutical composition containing the camptothecin compound and a pharmaceutically acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarially pure and non-toxic in the amounts used.

The compounds of the present invention may also be administered in the form of liposome or microvesicle preparations. Liposomes are microvesicles which encapsulate a liquid within lipid or polymeric membranes. Liposomes and methods of preparing liposomes are known and are described, for example, in U.S. Pat. No. 4,452,747, U.S. Pat. No. 4,448,765, U.S. Pat. No. 4,837,028, U.S. Pat. No. 4,721,612, U.S. Pat. No. 4,594,241, U.S. Pat. No. 4,302,459 and U.S. Pat. No. 4,186,183. The disclosures of these U.S. Pat. No. patents are incorporated herein by reference. Suitable liposome preparations for use in the present invention are also described in WO-9318749-A1, J-02056431-A and EP-276783-A.

The camptothecin compounds may be used individually to inhibit the growth of tumors. Alternatively, combinations of two or more camptothecin compounds may be used or combinations of one or more camptothecin compounds with one or more known anti-tumor compounds. When a camptothecin compound is combined with a conventional anti-tumor compound, the camptothecin compound will generally be present in an amount ranging from about 1–99 wt. %, preferably, 5–95 wt. % of the combined amount of camptothecin and conventional anti-tumor compound. The pharmaceutical compositions noted above may contain these combinations of compounds together with an acceptable carrier or diluent.

Other features of the invention will become apparent in the course of the following descriptions of exemplary embodiments which are given for illustration of the invention and are not intended to be limiting thereof.

EXAMPLES

Example 1
7-Methyl-20(S)-CPT

2-Nitro-acetophenone was reduced to the corresponding amino analog using $FeSO_2$ and $NH_4OH$ in boiling aq. EtOH. Friedlander condensation of the amino analog with the tricyclic ketone employing TsOH in refluxing toluene afforded the title compound as a pale yellow solid. 250 MHz NMR (DMSO-$d_6$) δ 0.90 (t, 3, J=7 Hz, H-18), 1.88 (m, 2, H-19), 2.79 (s, 3, 7-$CH_3$), 5.27 (s, 2, H-5), 5.43 (s, 2, H-17), 6.44 (s, 1, 20-OH), 7.35 (s, 1, H-14), 7.56–8.30 (m, 4, H-9, H-10, H-11, H-12).

Alternatively, the title compound can be generated by the treatment of a suspension of 20(S)-CPT in aq. EtOH containing $FeSO_4$ at 0° C. with conc. $H_2SO_4$ followed by 30% aq. $H_2O_2$ (see Sawada et al., 1991).

Example 2
7-Bromomethyl-20(S)-CPT

A stirred suspension of 7-methyl-20(S)-CPT in glac. HOAc was treated with 1.5 eq. NBS (N-bromosuccinimide) and 0.1 equivalent benzoyl peroxide at ambient temperature under fluorescent lighting. After 48 h, a mixture of starting material, unidentified side products, and the title compound was isolated by column chromatography ($SiO_2$, 1% MeOH/$CHCl_3$). 250 MHz $^1$H NMR (DMSO-$d_6$), δ 0.89 (3, t, J=7 Hz, H-18), 1.88 (2, m, H-19), 4.9 (2, s, 7-$CH_2Br$), 5.35 (2, s, H-5), 5.71 (2, s, H-17), 6.45 (1, s, 20-OH), 7.34 (1, s, H-14), 7.55–8.25 (4, m, H-9, H-10, H-11, and H-12).

Example 3
7-Iodomethyl-20(S)-CPT

The bromomethyl substrate from the preceding example was dissolved in DMF and treated with excess LiI. Evaporation of the solvent followed by chromatographic purification of the residue afforded the title compound as a yellow solid. 250 MHz NMR (DMSO-$d_6$) δ 0.89 (3, t, J=7 Hz, H-18), 1.88 (2, m, H-19), 4.82 (2, s, 7-$CH_2I$), 5.35 (2, s, H-5), 5.70 (2, s, H-17), 6.45 (1, s, 20-OH), 7.34 (1, s, H-14), 7.54–8.26 (4, m, H-9, H-10, H-11, and H-12).

Example 4
7-Bromomethyl-10,11-methylenedioxy-20(S)-CPT

7-Chloromethyl-10,11-methylenedioxy-20(S)-CPT was dissolved in DMF and treated with 1.5 equivalents of LiBr. The title compound resulted as a yellow solid after work-up involving solvent removal and chromatography. 250 MHz NMR (DMSO-$d_6$) δ 0.88 (t, 3, J=7 Hz, H-18), 1.85 (m, 2, H-19), 5.18 (s, 2, —$CH_2Br$), 5.33 (s, 2, H-5), 5.42 (s, 2, H-17), 6.35 (s, 2, $OCH_2O$), 6.53 (s, 1, OH), 7.20 (s, 1, H-14), 7.56 (s, 1, H-12), 7.72 (s, 1, H-9).

Example 5
7-Iodomethyl-10,11-methylenedioxy-20(S)-CPT

The preceding 7-chloromethyl compound was dissolved in DMF and treated with 1.5 equivalents of LiI. After removal of the solvent and chromatography of the residue, the title compound was obtained as a pale yellow solid. 250 MHz NMR (DMSO-$d_6$) δ 0.88 (t, 3, J=7 Hz, H-18), 1.85 (m, 2, H-19), 5.14 (s, 2, —$CH_2I$), 5.33 (s, 2, H-5), 5.43 (s, 2, H-17), 6.36 (s, 2, $OCH_2O$), 6.52 (s, 1, 20-OH), 7.18 (s, 1, H-14), 7.55 (s, 1, H-12), 7.70 (s, 1, H-9).

Example 6
7-Methyl-10 11-methylenedioxy-20(S)-CPT 3,4-Methylenedioxy-acetophenone was nitrated by portionwise addition to cold (0° C.) stirred conc. $HNO_3$. After 45 min the clear solution was poured into ice water and the 3,4-methylenedioxy-6-nitro-acetophenone was isolated as a yellow solid. Reduction using $FeSO_4$ in boiling aq. EtOH containing $NH_4OH$ provided 2-amino-4,5-methylenedioxy-acetophenone. Friedlander condensation of this compound with the tricyclic ketone in toluene containing HOAc and TSOH gave 7-methyl-10,11-methylenedioxy-20(S)-CPT as a beige solid. 250 MHz $^1$H NMR (DMSO-$d_6$) δ 0.87 (t, 3, J=7 Hz, H-18), 1.87 (m, 2, H-19), 2.64 (s, 3,7-$CH_3$), 5.14 (s, 2, H-5), 5.40 (s, 2, H-17), 6.27 (s, 2, $OCH_2O$), 6.48 (s, 1, OH), 7.21 (s, 1, H-14), 7.47 (s, 1, H-9), 7.53 (s, 1, H-12).

Example 7
7-Bromomethyl-10,11-methylenedioxy-20(S)-CPT

Treatment of the substrate obtained in Example 6 with NBS and benzoyl peroxide in HOAc afforded the target compound of Example 4. The physical properties were the same as those obtained by the alternate synthesis.

Example 8
7-Methyl-10,11-ethylenedioxy-20(S)-CPT, 7-Bromomethyl-10,11-ethylenedioxy-20(S)-CPT 3,4-Ethylenedioxy-acetophenone was nitrated employing fuming $HNO_3$ in conc. $H_2SO_4$ at 0° C. Reduction of this 3,4-ethylenedioxy-6-nitro-acetophenone product with $FeSO_4$ and conc. $NH_4OH$ in hot aq. EtOH gave 2-amino-3,4-ethylenedioxy-acetophenone. In a manner analogous to Example 8, the above compound underwent facile Friedlander condensation with the tricyclic ketone in toluene containing HOAC and TSOH to afford the title compound as a tan powder (>50%) after chromatographic clean-up ($SiO_2$, 1% MeOH/$CHCl_3$). 250 MHz $^1$H NMR (DMSO-$d_6$) δ 0.88 (t, 3, J=7 Hz, H-18), 1.88 (m, 2, H-19), 264 (s, 3, 7-$CH_3$), 4.42 (s, 4, O($CH_2)_2$O), 5.14 (s, 2, H-5), 5.40 (s, 2, H-17), 6.48 (s, 1, 20-OH), 7.24 (s, 1. H-14), 7.48 (s, 1, H-9), 7.50 (s, 1, H-12).

Alternatively, the title compound can be prepared by treatment at 0° C. of a suspension of 10,11-ethylenedioxy-20(S)-CPT in aq. EtOH containing $FeSO_4$ with conc. $H_2SO_4$, followed by 30% aq. $H_2O_2$.

Bromination as described in Example 2 above affords electrophile 7-bromomethyl-10,11-ethylenedioxy-20(S)-CPT.

Example 9
7-Methyl-10-nitro-20(S)-CPT, 7-Methyl-10-amino-20(S)-CPT, and 7-Methyl-10-chloro-20(S)-CPT, and 7-Bromomethyl Derivatives The title nitro compound can be prepared by Friedlander reaction of the tricyclic ketone and the appropriate 2-amino-acetophenone derivative. It is preferred, however, to subject the readily available nitro-CPT substrate to nucleophilic free radical methylation. Thus a stirred suspension of 10-nitro-20(S)-CPT in aq. EtOH at 0° C. was treated sequentially with $FeSO_4$, conc. $H_2SO_4$ and then 30% aq. $H_2O_2$. The desired 7-methyl-10-nitro-20(S)-CPT was separated from the polar 7-hydroxymethyl side product by $SiO_2$ chromatography (0.5% MeOH/$CHCl_3$). 250 MHz $^1$H NMR (DMSO-d$_6$) δ 0.88 (3, t, J=7 Hz, H-18), 1.88 (2, m, H-19), 3.01 (3, s, 7-CH$_3$), 5.37 (2, s, H-5), 5.46 (2, s, H-17), 6.52 (1, s, 20-OH), 7.42 (1, s, H-14), 8.41 (1, d, J=7 Hz, H-12), 8.53 (1, dd, J=2, 7 Hz, H-11), 9.06 (1, d, J=2 Hz, H-9).

Reduction of the nitro group by SnCl$_2$ as described above provided the title amine as a yellow-orange powder. 250 MHz $^1$H NMR (DMSO-d$_6$) δ 0.88 (3, t, J=7 Hz, H-18), 1.86 (2, m, J=7 Hz, H-19), 2.77 (3, s, 7-CH$_3$), 5.16 (2, s, H-5), 5.38 (2, s, H-17), 6.88 (1, d, J=2 Hz, H-9), 7.19 (1, s, H-14), 7.20 (1, dd, J=2, 7 Hz, H-11), 7.83 (1, d, J=7 Hz, H-12).

The amino compound was diazotized at 0° C. using NaNO$_2$ in conc. HCl. CuCl was added and the mixture warmed at 50° C. After 20 min, the 10-chloro analog was isolated upon quenching the reaction over ice. 250 MHz $^1$H NMR (DMSO-d$_6$) δ 0.89 (3, t, J=7 Hz, H-18), 1.87 (2, m, H-19), 2.91 (3, 5, 7-CH3), 5.26 (2, s, 2, H-5), 5.42 (2, s, H-17), 6.50 (1, s, 20-OH), 7.29 (1, s, H-14), 7.81 (1, dd, J=2, 7 Hz, H-11), 8.15 (1, d, J=7 Hz, H-12), 8.20 (1, d, J=2 Hz, H-9).

As set forth earlier, free radical bromination provides other title compounds.

Example 10
7-Methyl-9-nitro-20(S)-CPT, 7-Bromomethyl-9-nitro-20(S)-CPT, and 9-Amino-7-bromomethyl-20(S)-CPT The nitro compound can be prepared by Friedlander condensation of the tricyclic ketone with 2-amino-6-nitroacetophenone or by the nitration of 7-methyl-20(S)-CPT followed by separation of the 9- and 12-nitro isomers. It is preferred, however, to methylate the more readily available 9-nitro-20(S)-CPT under radical substitution conditions. Thus 9-nitro-20(S)-CPT was treated at 0° C. as a stirred suspension in aq. EtOH with FeSO$_4$ and conc. H$_2$SO$_4$ followed by 30% H$_2$O$_2$. The compound was separated from the more polar 7-hydroxymethyl side-product by chromatography (SiO$_2$, MeOH/CHCl$_3$). 250 MHz $^1$NMR (DMSO-d$_6$) δ 0.92 (3, t, J=7 Hz, H-18), 1.91 (2, m, H-19), 3.07 (3, s, 7-CH$_3$), 5.31 (2, s, H-5), 5.42 (2, s, H-17), 6.49 (1, s, OH), 7.37 (1, s, H-14), 8.01 (1, t, J=7 Hz, H-11), 8.49–8.55 (2, m, H-10 and H-12). Free radical bromination of the preceding substrate under conditions set forth in Example 2 above gave the bromomethyl derivative.

The nitro compound was treated at 0° C. as a stirred solution in conc. HCl with excess SnCl$_2$. The title amine compound precipitated over the course of 3 h contaminated with tin salts. The amine was separated from salts by extraction into DMF. Recrystallization from DMF/Et$_2$O gave purified compound. 250 MHz $^1$H NMR (DMSO-d$_6$) δ 0.98 (3, t, J=7 Hz, H-18), 1.88 (2, m, H-19), 2.60 (3, s, 7-CH$_3$), 5.29 (2, s, H-5), 5.44 (2, s, H-17), 6.13 (2, br s, 9-NH$_2$), 6.53 (1, s, 20-OH), 6.83 (1, d, H=7 Hz, H-10), 7.31 (1, s, H-14), 7.33 (1, d, J=7 Hz, H-12), 7.54 (1, t, J=7 Hz, H-11).

Example 12
7-Methyl-10,11-methylenedioxy-9-nitro-20(S)-CPT, 9-Amino-7-methyl-10,11-methylenedioxy-20(S)-CPT and 7-Bromomethyl Derivative The title nitro compound can be prepared by radical substitution conditions as described in the preceding example employing 9-nitro-10,11-methylenedioxy-20(S)-CPT. The preferred method is direct nitration of readily-synthesized 7-methyl-10,11-MD-20(S)CPT. Thus this compound was dissolved in conc. H$_2$SO$_4$ over several min. The clear red-brown solution was warmed to ambient temperature and poured over ice after 3 h. The title nitro compound separated as a yellow solid. 250 MHz $^1$H NMR (DMSO-d$_6$) δ 0.87 (3, t, J=7 Hz, H-18), 1.86 (2, m, H-19), 2.85 (3, s, 7-CH$_3$), 5.24 (2, s, H-5), 5.42 (2, s, H-17), 6.52 (2, s, OCH$_2$O), 7.25 (1, s, H-14), 7.81 (1, s, H-12).

The nitro compound was reduced by SnCl$_2$ as described in the preceding example to afford the title amine as a yellow solid. 250 MHz $^1$H NMR (DMSO-d$_6$) δ 0.86 (3, t, J=7 Hz, H-18), 1.84 (2, m, H-19), 2.52 (3, s, 7-CH$_3$), 5.20 (2, s, H-5), 5.40 (2, s, H-17), 5.74 (2, br s, 9-NH$_2$), 6.16 (2, s, 10,11-OCH$_2$O), 6.47 (1, s, 20-OH), 6.90 (1, s, H-14), 7.21 (1, s, H-12).

Free radical bromination as described in earlier examples affords the 7-bromomethyl analogs.

Example 13
10,11-Ethylenedioxy-7-methyl-9-nitro-20(S)-CPT, 9-Amino-10,11-ethylenedioxy-7-methyl-20(S)-CPT, and 7-Bromomethyl Derivatives The title nitro compound may be synthesized from 9-nitro-10,11-ethylenedioxy-20(S)-CPT by radical methylation as described in Example 12 above. The preferred route of synthesis, however, is by direct nitration of the preformed 7-methyl- 10,11-EDO-20(S)-CPT. Thus a stirred solution of this compound in conc. H$_2$SO$_4$ at –10° C. was treated dropwise over several min with a slight excess of conc. HNO$_3$ in conc. H$_2$SO$_4$. After the addition, the stirred red solution was warmed to ambient temperature and after 2 h the mixture was poured over ice. The 9-nitro compound was separated from some 12-nitro isomer by column chromatography (SiO$_2$, gradient 0.1% MeOH/CHCl$_3$ to 0.4% MeOH/CHCl$_3$). 250 MHz $^1$H NMR (DMSO-d$_6$) δ 0.87 (3, t, J=7 Hz, H-18), 1.85 (2, m, H-19), 2.87 (3, s, 7-CH$_3$), 4.57 (4, m, O(CH$_2$)$_2$O), 5.16 (2, s, H-5), 5.40 (2, s, H-17), 6.51 (1, s, 20-OH), 7.28 (1, s, H-14), 7.79 (1, s, H-12).

Reduction of the nitro group with SnCl$_2$ in the usual manner provided the corresponding amine. 250 MHz $^1$NMR (DMSO-d$_6$) 0.86 (3, t, J=7 Hz, H-18), 1.85 (2, m, H-19), 2.54 (3, s, 7-CH$_3$), 4.27 (4, m, O(CH$_2$)$_2$O, 5.12 (2, s, H-5), 5.39 (2, s, H-17), 6.50 (1, s, 20-OH), 6.98 (1, s, H-14), 7.22 (1, s, H-12).

As before, free radical bromination provided the 7-bromomethyl analogs.

Example 14
7-Methyl-9-chloro-20(S)-CPT and 7-Bromomethyl-9-chloro-20(S)-CPT

The first title compound can be synthesized directly by Friedlander condensation of the appropriate amino acetophenone with the tricyclic ketone. A more convenient method, however, involves conversion of the readily prepared 9-amino-7-methyl-20(S)-CPT as follows: A stirred orange solution of 9-amino-7-methyl-20(S)-CPT (377 mg, 1.00 mmol) in conc. HCl (10 ml) at 0° C. was treated with NaNO$_2$ (96 mg, 1.39 mmol) in H$_2$O (0.5 ml) over 2 min. The tan mixture was treated with CuCl (192 mg, 1.94 mmol) and heated at 50° C. for 10 min. The mixture was poured over ice and the crude chloro compound was collected. This was combined with a CHCl$_3$ extract of the aq. filtrate and chromatographed (SiO$_2$, 0.5% MeOH/CHCl$_3$) to provide pure title compounds as an off-white solid in 60% yield. 250 MHz $^1$H NMR (DMSO-d$_6$) δ 0.88 (3, t, J=7 Hz, H-18), 1.87 (2, m, H-19), 2.67 (3, s, 7-CH$_3$), 5.29 (2, s, H-5), 5.45 (2, s, H-17), 6.51 (1, s, 20-OH), 7.32 (1, s, H-14), 7.49 (1, d, J=7 Hz, H-12), 7.86 (1, t, J=7 Hz, H-11), 8.15 (1, d, J=7 Hz, H-10); $[\alpha]_D^2$+19° (c 0.6, MeOH-CHCl$_3$).

Free radical bromination gives the bromomethyl analog.

Example 15
7-Methyl-9-chloro-10,11-methylenedioxy-20(S)-CPT and its 7-Bromomethyl Derivative The title compound was prepared via the diazonium salt from the amine of Example 12 by reaction with CuCl as described in the preceding example. 250 Mhz $^1$H NMR (DMSO-d$_6$) δ 0.88 (3, t, J=7 Hz, H-18), 1.07 (2, m, H-19), 2.69 (3, s, 7-CH₃), 5.22 (2, s, H-5), 5.41 (2, s, H-17), 6.35 (2, s, OCH₂O), 6.50 (1, s, 20-OH), 7.23 (1, s, H-14), 7.42 (1, s, H-12).

The usual free radical bromination affords the bromomethyl analog.

Example 16
7-Methyl-9-chloro-10,11-ethylenedioxy-20(S)-CPT and its 7-Bromomethyl Analog Similar to Example 15, the amine of Example 13 was diazotized with NaNO₂ in cold conc. HCl and then underwent Sandmeyer reaction with CuCl to afford the chloro derivative. 250 MHz $^1$H NMR (DMSO-d₆) δ 0.87 (3, t, J=7 Hz, H-18), 1.87 (2, m, H-19), 2.74 (3, s, 7-CH₃), 4.48 (4, m, O(CH₂)₂O), 5.20 (2, s, H-5), 5.39 (2, s, H-17), 6.50 (1, s, 20-OH), 7.14 (1, s, H-14), 7.52 (1, S, H-12).

The 7-bromomethyl analog was obtained similarly.

Example 17
7-Methanesulfonyloxymethyl-20(S)-CPT

7-Hydroxymethyl-20(S)-CPT was prepared by the method of Sawada et al., 1991. A solution of this compound (378 mg, 1.00 mmol) in dry pyridine (50 mL) was cooled to 0° C. and treated dropwise over several minutes with methanesulfonyl chloride (20% mole excess). After 24 h, the mixture was filtered and distilled under high vacuum at ambient temperature. The residue was triturated with cold dry CH₂CH₂ to give the title compound as a yellow solid (60%): mp decomp >75° C.; 250 MHz $^1$H NMR (CDCl₃) δ 1.07 (3, t, J=7 Hz, H-18), 1.93 (2, m, H-19), 5.35 (1, d, J=17 Hz, H-17), 5.85 (1, d, J=17 Hz, H-17), 5.95 (2, s, H-5), 6.10 (2, s, 7-CH₂X), 7.5–8.5 (5, m, aromatic).

Example 18
7-Trifluoromethanesulfonyloxymethyl-20(S)-CPT

A stirred solution of 7-hydroxymethyl-20(S)-CPT (189 mg, 0.50 mmol) in dry pyridine (30 mL) at 0° C. was treated over 3 min with a 20% molar excess of triflic anhydride. After warming to ambient temperature over 2 h, the solvent was removed under high vacuum. The residue was triturated with cold toluene to give the title compound as a yellow thermally unstable compound (65%); 250 MHz NMR (CDCl₃) δ 1.07 (3, t, J=7 Hz, H-18), 1.93 (2, m, H-19), 5.45 (1, d, J=17 Hz, H-17), 5.93 (1, d, J=17 Hz, H-17), 6.05 (2, s, H-5), 6.24 (2, s, 7-CH₂X), 7.5–8.5 (5, m, aromatic).

Alternatively, a unique method for the preparation of the title compound from the 7-chloromethyl substrate was realized by an adaptation of procedures of Gramstad and Haszeldine, 1956. Thus silver triflate (257 mg, 1.00 mmol) was suspended in stirred anhydrous (anh) dioxane (25 mL) and treated over 3 min with a solution of 7-chloromethyl-20(S)-CPT (0.75 mmol) in anh dioxane. The mixture was heated at 50° C. for 30 min, cooled, and filtered to remove AgCl. Evaporation of the dioxane under reduced pressure at ambient temperature gave the title compound.

Example 19
7-Nonafluorobutanesulfonyloxymethyl-20(S)-CPT

As in Example 18, a stirred solution of 7-hydroxymethyl-20(S)-CPT in pyridine at 0° C. was treated dropwise with a 20% molar excess of nonafluorobutanesulfonic anhydride. The mixture was stirred at ambient temperature for 1 h, and the solvent removed at ambient temperature. Trituration of the residue with cold toluene gave the title compound as a yellow solid (60%): mp >60° (decomp.).

Alternatively, as in Example 18, the title compound resulted by the action of silver nonafluorobutanesulfonate on 7-chloromethyl-20(S)-CPT in dioxane.

Example 20
7-(p-toluenesulfonyloxy)methyl-20(S)-CPT

In the same fashion as described for methods in Examples 18 and 19, reaction of silver p-toluenesulfonate and 7-chloromethyl-20(S)-CPT affords the title compound as a crystalline yellow solid; 250 MHz NMR (CDCl₃) δ 1.05 (3, t, J=7 Hz, H-18), 1.92 (2, m, H-19), 2.54 (3, s, X-CH₃), 5.43 (1, d, J=17 Hz, H-17), 5.92 (1, d, J=17 Hz, H-17), 6.01 (2, s, H-5), 6.20 (2, s, 7-CH₂X), 7.3–8.5 (9, m, aromatic).

Example 21
9-Chloromethyl-20(S)-CPT

9-Bromo-20(S)-CPT was prepared as described in the literature (Wall et al., 1993, J. Med. Chem., 36:2689). This compound (120 mg, 0.28 mmol) was refluxed with excess CuCN (500 mg) in dry DMF for 5 h. Chromatographic purification (SiO₂) afforded 9-cyano-20(S)-CPT as a yellow solid (37 mg, 35%). 250 MHz NMR (DMSO-d₆) δ 0.90 (t, 3, J=7 Hz, H-18), 1.89 (m, 2, H-19), 5.25 (s, 2, H-5), 5.40 (s, 2, H-17), 6.51 (s, 1, 20-OH), 7.32 (s, 1, H-14), 8.17 (d, 1, J=8.5 Hz, H-12), 8.19 (t, 1, J=8.5 Hz, H-11), 8.52 (d, 1, J=8.5 Hz, H-10), 8.78 (s, 1, H-7).

9-cyano-20(S)-CPT (160 mg, 0.40 mmol) was refluxed for 24 hr in a mixture of 2N HCl (15 ml) and EtOH (150 ml). The solvent was evaporated to give the crude acid intermediate, 9-carboxy-20(S)-CPT. 250 MHz NMR (DMSO-d₆) δ 0.89 (t, 3, J=7 Hz, H-18), 1.87 (m, 2, H-19), 5.27 (s, 2, H-5), 5.41 (s, 2, H-17), 7.34 (s, 1, H-14), 7.54 (d, 1, H-12), 7.85 (t, 1, H-11), 8.21 (d, 1, H-10), 8.82 (s, 1, H-7).

The carboxy analog (39 mg, 0.10 mmol) was treated in THF (2 ml) with B₂H₆/THF (1.0 M, 0.25 ml, 0.25 mmol) over 5 min. at room temperature (RT). Appropriate workup of the reaction gave 9-hydroxymethyl-20(S)-CPT (80%) as a pale yellow solid. 250 MHz NMR (DMSO-d₆) δ 0.88 (t, 3, J=7 Hz, H-18), 1.87 (m, 2, H-19), 4.88 (d, 2, J=4 Hz, 9-CH₂OH), 5.32 (s, 2, H-5), 5.65 (s, 2, H-17), 5.80 (t, 1, J=4 Hz, 9-CH₂OH), 6.49 (s, 1, 20-OH), 7.29 (s, 1, H-14), 7.65 (t, 1, J=7 Hz, H-11), 8.01 (d, 1, J=7 Hz, H-12), 8.17 (d, 1, J=7 Hz, H-10), 8.70 (s, 1, H-7).

9-hydroxymethyl-20(S)-CPT (30 mg) was heated at 80° C. with a 1.5 eq. mixture of Ph₃P-CCl₄ in DMF (2 ml) for 6 h. Workup gave 9-chloromethyl-20(S)-CPT (73%) as a pale yellow solid. 250 MHz NMR (DMSO-d₆) δ 0.87 (t, 3, J=7 Hz, H-18), 1.87 (m, 2, H-19), 4.79 (s, 2, 9-CH₂Cl), 5.33 (s, 2, H-5), 5.63 (s, 2, H-17), 6.50 (s, 1, 20-OH), 7.29 (s, 1, H-14), 7.66 (t, 1, J=7 Hz, H-11), 8.01 (d, 1, J=7 Hz, H-12), 8.16 (d, 1, J=7 Hz, H-10), 8.68 (s, 1, H-7).

Example 22
9-Bromomethyl-20(S)-CPT

The preceding 9-chloromethyl compound was dissolved in DMF and treated with 1.5 eq of LiBr. The solvent was evaporated and the residue chromatographed to give the title compound as a yellow solid. 250 MHz NMR (DMSO-d₆) δ 0.87 (t, 3, J=7 Hz, H-18), 1.88 (m, 2, H-19), 4.61 (s, 2, 9-CH₂Br), 5.32 (s, 2, H-5), 5.63 (s, 2, H-17), 6.51 (s, 1 20-OH), 7.29 (s, 1, H-14), 7.65 (t, 1, J=7 Hz, H-11), 8.00 (d, 1, J=7 Hz, H-12), 8.14 (d, 1, J=7 Hz, H-10), 8.67 (s, 1, H-7).

Alternatively, the title compound can be prepared from 9-methyl-20(S)-CPT (Wall et al., 1993) by reaction with 1.5 eq NBS and 0.1 eq benzoyl peroxide under fluorescent lighting at RT. A low yield (22%) of the product resulted after chromatography.

Example 23
9-Iodomethyl-20(S)-CPT

9-Chloromethyl-20(S)-CPT (20 mg) was dissolved in DMF (1 ml) and treated with 1.5 eq LiI. Chromatographic purification on SiO$_2$ gave 14 mg of title compound as a dark yellow solid. 250 MH NMR (DMSO-d$_6$) δ 0.89 (3, t, J=7 Hz, H-18), 1.88 (2, m, H-19), 4.15 (2, s, 9-CH$_2$I), 5.27 (s, 2, H-5), 5.62 (s, 2, H-17), 6.50 (s, 1, 20-OH), 7.28 (s, 1, H-11), 7.61 (t, 1, J=7 Hz, H-11), 7.92 (d, 1, J=7 Hz, H-12), 8.04 (d, 1, J=7 Hz, H-10), 8.61 (s, 1, H-7).

Example 24
10-Chloromethyl-20(S)-CPT

10-Carboxy-20(S)-CPT (Wall et al., 1993) was converted to 10-hydroxymethyl-20(S)-CPT by the method detailed in Example 1 (65%). 250 MHz NMR (DMSO-d$_6$), δ 0.88 (t, 3, J=7 Hz, H-18), 1.87 (m, 2, H-19), 4.90 (d, 2, J=4 Hz, 10-CH$_2$OH), 5.29 (s, 2, H-5), 5.64 (s, 2, H-17), 5.77 (t, 1, J=4 Hz, 10-CH$_2$OH), 6.50 (s, 1, 20-OH), 7.25 (s, 1, H-14), 7.92 (d, 1, J=8 Hz, H-12), 8.22 (d, 1, J=8 Hz, H-11), 8.39 (s, 1, H-9), 8.51 (s, 1, H-7).

Reaction of this material with 1.5 eq Ph$_3$P-CCl$_4$ in DMF at 80° C. gave a 72% yield of 10-chloromethyl-20(S)-CPT. 250 MHz NMR (DMSO-d$_6$) δ 0.88 (t, 3, J=7 Hz, H-18), 1.87 (m, 2, H-19), 4.74 (s, 2, 10-CH$_2$Cl), 5.34 (s, 2, H-5), 5.63 (s, 2, H-17), 6.50 (s, 1, 20-OH), 7.23 (s, 1, H-14), 7.89 (d, 1, J=8 Hz, H-12), 8.15 (d, 1, J=8 Hz, H-11), 8.32 (s, 1, H-9), 8.45 (s, 1, H-7).

Example 25
10-Bromomethyl and 10-Iodomethyl-20(S)-CPT

Reaction of 10-chloromethyl-20(S)-CPT with excess LiBr in DMF gave 10-bromo-20(S)-CPT (81%). 250 MHz NMR (DMSO-d$_6$) δ 0.87 (t, 3, J=7 Hz, H-18), 1.89 (m, 2, H-19), 4.65 (s, 2, 10-CH$_2$Br), 5.31 (s, 2, H-5), 5.63 (s, 2, H-17), 6.49 (s, 1, 20-OH), 7.28 (s, 1, H-14), 7.77 (d, 1, J=8 Hz, H-12), 8.04 (d, 1, J=8 Hz, H-11), 8.23 (s, 1, H-9), 8.43 (s, 1, H-7).

Reaction of 10-chloromethyl-20(S)-CPT with LiI under similar circumstances as above gave 10-iodomethyl-20(S)-CPT. 250 MHz NMR (DMSO-d$_6$) δ 0.87 (t, 3, J=7 Hz, H-18), 1.88 (m, 2, H-19), 4.14 (s, 2, 10-CH$_2$I), 5.30 (s, 2, H-5), 5.62 (s, 2, H-17), 6.49 (s, 1, 20-OH), 7.28 (s, 1, H-14), 7.75 (d, 1, J=8 Hz, H-12), 8.01 (d, 1, J=8 Hz, H-11), 8.21 (s, 1, H-9), 8.43 (s, 1, H-7).

Example 26
11-Chloromethyl-20(S)-CPT

11-Hydroxymethyl-20(S)-CPT (Wani et al., 1987, J. Med. Chem., 30:1774) was converted to the title compound in 65% yield by the method given in Example 24. 250 MHz NMR (DMSO-d$_6$) δ 0.88 (t, 3, J=7 Hz, H-18), 1.87 (m, 2, H-19), 4.72 (s, 2, 11-CH$_2$Cl), 5.35 (s, 2, H-5), 5.63 (s, 2, H-17), 6.48 (s, 1, 20-OH), 7.23 (s, 1, H-14), 7.89 (d, 1, J=8 Hz, H-9), 8.17 (d, 1, J=8 Hz, H-10), 8.29 (s, 1, H-12), 8.47 (s, 1, H-7).

Example 27
11-Bromomethyl- and 11-Iodomethyl-20(S)-CPT

Reaction of 11-chloromethyl-20(S)-CPT with LiBr as in Example 25 gave the corresponding 11-bromomethyl-20(S)-CPT (77%) and reaction with LiI gave 11-iodomethyl-20(S)-CPT (65%).

Example 28
12-Chloromethyl-,12-Bromomethyl- and 12-Iodomethyl-20(S)-CPT

12-Carboxy-20(S)-CPT was prepared as described in the literature (Pau et al., 1975, Acta Chimica Sinica, 33:71) and reduced with B$_2$H$_6$ as described in Example 21 for the 9-carboxy isomer to give 12-hydroxymethyl-20(S)-CPT as a light yellow solid (68%).

The above intermediate was treated at 80° C. with Ph$_3$P-CCl$_4$ in DMF as described in Example 21 to afford 12-chloromethyl-20(S)-CPT (82%). 250 MHz NMR (DMSO-d$_6$) δ 0.88 (t, 3, J=7 Hz, H-18), 1.87 (m, 2, H-19), 4.83 (s, 2, 12-CH$_2$Cl), 5.35 (s, 2, H-5), 5.63 (s, 2, H-17), 6.49 (s, 1, 20-OH), 7.26 (s, 1, H-14), 7.70 (t, 1, J=7 Hz, H-10), 8.08 (d, 1, J=7 Hz, H-9), 8.27 (d, 1, J=7 Hz, H-11), 8.69 (s, 1, H-7).

As described in preceding examples, the 12-chloromethyl compound was converted to 12-bromomethyl-20(S)-CPT (77%) and 12-iodomethyl-20(S)-CPT (65%).

Example 29
9-Methanesulfonyloxymethyl-20(S)-CPT

9-Hydroxymethyl-20(S)-CPT (cf. Example 21, 37.8 mg, 0.10 mmol) was dissolved/suspended in dry pyridine (Py) (5 ml) and cooled to 0° C. Methanesulfonyl chloride (20% mole excess) was added over 3 min. After stirring overnight, the mixture was filtered, and the filtrate was concentrated to dryness under high vacuum at RT. The oily residue gave the title compound as a crystalline yellow solid (67%) upon trituration with CH$_2$Cl$_2$. 250 MHz NMR (CDCl$_3$) δ 1.05 (t, 3, J=7 Hz, H-18), 1.91 (m, 2, H-19), 3.10 (s, 3, —SO$_2$Me), 5.34 (d, 1, J=17 Hz, H-17), 5.86 (d, 1, J=17 Hz, H-17), 5.88 (s, 2, H-5), 6.04 (s, 2, 9-CH$_2$ OSO$_2$Me), 7.2–8.5 (m, 5, arom H).

Example 30
10-, 11-, and 12-Methanesulfonyloxymethyl-20(s)-CPT Analogs

Reactions of 10-, 11-, and 12-hydroxymethyl-20(S)-CPT analogs from Examples 24, 26, and 28, respectively, with methanesulfonyl chloride, as described in the preceding example, gave the title mesylate esters in good yields.

Example 31
9-Trifluoromethanesulfonyloxymethyl-20(S)-CPT

A stirred solution of 9-hydroxymethyl-20(S)-CPT (189 mg, 0.05 mmol) in dry Py (30 ml) at 0° C. was treated over ~3 min with triflic anhydride (20% molar excess). The stirred mixture was warmed to RT over 2 h and concentrated to dryness at RT under high vacuum to afford a gummy solid. Trituration with cold toluene gave the unstable title compound as a pale yellow solid (62%). 250 MH NMR (CDCl$_3$) δ 1.07 (t, 3, J=7 Hz, H-18), 1.93 (m, 2, H-19), 5.45 (d, 1, J=17 Hz, H-17), 5.92 (d, 1, J=17 Hz, H-17), 5.99 (s, 2, H-5), 6.25 (s, 2, 9-CH$_2$OSO$_2$CF$_3$), 7.51 (t, 1, J=7 Hz, H-11), 7.66 (d, 1, J=7 Hz, H-12), 7.95 (d, 1, J=7 Hz, H-10), 8.55 (s, 1, H-7).

Alternatively, the title ester was prepared from 9-chloromethyl-20(S)-CPT by reaction with silver triflate. Thus a stirred suspension of silver triflate (257 mg, 1.00 mmol) in anhydrous (anh) dioxane (25 ml) was treated over 3 min with a solution of CPT substrate (0.75 mmol) in anh dioxane. The mixture was heated for 30 min at 50° C., cooled, and filtered. The dioxane was evaporated and the residue triturated with toluene to provide >50% yield of the triflate ester.

Example 32
10-, 11-, and 12-Trifluoromethanesulfonyl-oxymethyl-20 (S)-CPT Analogs In analogy to the preceding example, the title triflate esters were prepared from both the corresponding hydroxymethyl CPT compounds and the chloromethyl-CPT analogs.

Example 33

9-, 10-, and 12-Nonafluorobutane-sulfonyloxymethyl-20(S)-CPT Analogs

By reactions similar to the preceding example, the title nonaflate esters were obtained. Thus, for 9 substitution, 9-hydroxymethyl-20(S)-CPT as a stirred solution in anh pyridine (Py) at 0° C. was treated dropwise with nonafluorobutanesulfonic anhydride (20% molar excess). After stirring at RT for 1 h, the solvent was removed under reduced pressure at ambient temperature. The oily residue was triturated with cold toluene to give 9-nonafluorobutanesulfonyloxymethyl-20(S)-CPT (55%) as a pale yellow, thermally unstable solid. Alternatively, treatment of 9-chloromethyl-20(S)-CPT with silver nonafluorobutanesulfonate in warm dioxane afforded the same product in 61% yield.

Example 34

9-, 10-, 11-, and 12-(p-toluenesulfonyloxy)methyl-20(S)-CPT Analogs

Following methods described in previous examples, reactions of 9-, 10-, 11-, and 12-chloromethyl-20(S)-CPT analogs with excess silver p-tosylate afforded the respective title analogs in yields from 52–75%. For 9-(p-toluenesulfonyloxy)methyl-20(S)-CPT the following 250 MHz NMR (CDCl$_3$) was recorded: δ 1.03 (t, 3, J=7 Hz, H-18), 1.92 (m, 2, H-19), 2.55 (s, 3, tosyl-CH$_3$), 5.39 (d, 1, J=17 Hz, H-17), 5.88 (d, 1, J=17 Hz, H-17), 5.98 (s, 2, H-5), 6.18 (s, 2, 9-CH$_2$-tosyl), 7.3–8.5 (9, aromatic H).

It is understood that the preceding representative examples may be varied within the scope of the present specification, both as to the reactants and conditions, by one skilled in the art to achieve essentially the same results.

As many apparently widely different embodiments of the present invention may be made without departing from the spirit and scope thereof, it is to be construed that the present invention is not limited to the specific embodiments thereof as defined in the appended claims.

What is claimed as new and desired to be secured by Letters Patent of the United States is:

1. A method of treating tumors susceptible to CPT in a mammal in need thereof, comprising administering to said mammal an effective amount for treating said tumors susceptible to CPT, with a 20(S)-camptothecin compound having the formula:

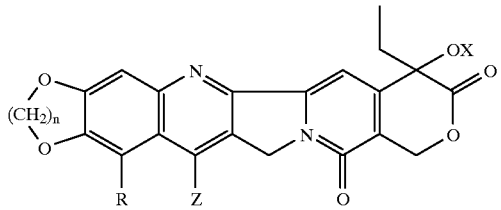

wherein

R is H, OH, NO$_2$, NH$_2$, N$_3$, halogen, COOH, O—C$_{1-3}$ alkyl, SH, S—C$_{1-3}$alkyl, CN, CH$_2$NH$_2$, NH—C$_{1-3}$alkyl, CH$_2$—NH—C$_{1-3}$alkyl, N(C$_{1-3}$ alkyl)$_2$, CH$_2$N(C$_{1-3}$alkyl)$_2$, O—, NH— and S—CH$_2$CH$_2$N(CH$_2$CH$_2$OH)$_2$, O—, NH— and S—CH$_2$CH$_2$CH$_2$N(CH$_2$CH$_2$OH)$_2$, O—, NH— and S—CH$_2$CH$_2$N(CH$_2$CH$_2$CH$_2$OH)$_2$, O—, NH— and S—CH$_2$CH$_2$CH$_2$N(CH$_2$CH$_2$CH$_2$OH$_2$)$_2$, O—, NH— and S—CH$_2$CH$_2$N(C$_{1-3}$alkyl)$_2$, O—, NH— and S—CH$_2$CH$_2$CH$_2$N(C$_{1-3}$alkyl)$_2$, CH$_2$—L or C$_{1-3}$ alkyl;

Z is CH$_2$—L, wherein L is a functional group selected from the group consisting of Cl, Br, I, C$_{1-30}$ alkyl-SO$_2$—, C$_{1-30}$ perfluoroalkyl-SO$_2$— and C$_{6-18}$ aryl-SO$_2$—;

X is H or OC(O)CHR$^5$NR$^3$R$^4$, where R$^5$ is the side chain of a naturally occurring α-amino acid and R$^3$ and R$^4$ are, independently, hydrogen or C$_{1-8}$ alkyl;

n is an integer of 1 or 2, or a pharmaceutically acceptable salt thereof.

2. The method of claim 1, wherein n=1.

3. The method of claim 1, comprising administering 1–60 mg/kg body weight per week of camptothecin ester.

4. The method of claim 1, wherein said administering is oral or parenteral administering.

* * * * *